United States Patent [19]

Goldberg et al.

[11] Patent Number: 4,874,360
[45] Date of Patent: Oct. 17, 1989

[54] URETERAL STENT SYSTEM

[75] Inventors: Jay R. Goldberg, Northbrook, Ill.; Donald V. Hillegass, Franksville, Wis.

[73] Assignee: Medical Engineering Corporation, Racine, Wis.

[21] Appl. No.: 214,180

[22] Filed: Jul. 1, 1988

[51] Int. Cl.[4] ............................................ A61M 25/00
[52] U.S. Cl. .......................................... 604/8; 604/281
[58] Field of Search ........................................ 604/8–10, 604/281, 282

[56] References Cited

U.S. PATENT DOCUMENTS 4,212,304  7/1980  Finney .................................... 604/8
4,671,795  6/1987  Mulchin ............................... 604/281

Primary Examiner—Dalton L. Truluck
Attorney, Agent, or Firm—Quarles & Brady

[57] ABSTRACT

A ureteral stent has a main body that is soft and flexible and a proximal hook portion which is stiffer to minimize expulsion from the kidney.

1 Claim, 3 Drawing Sheets

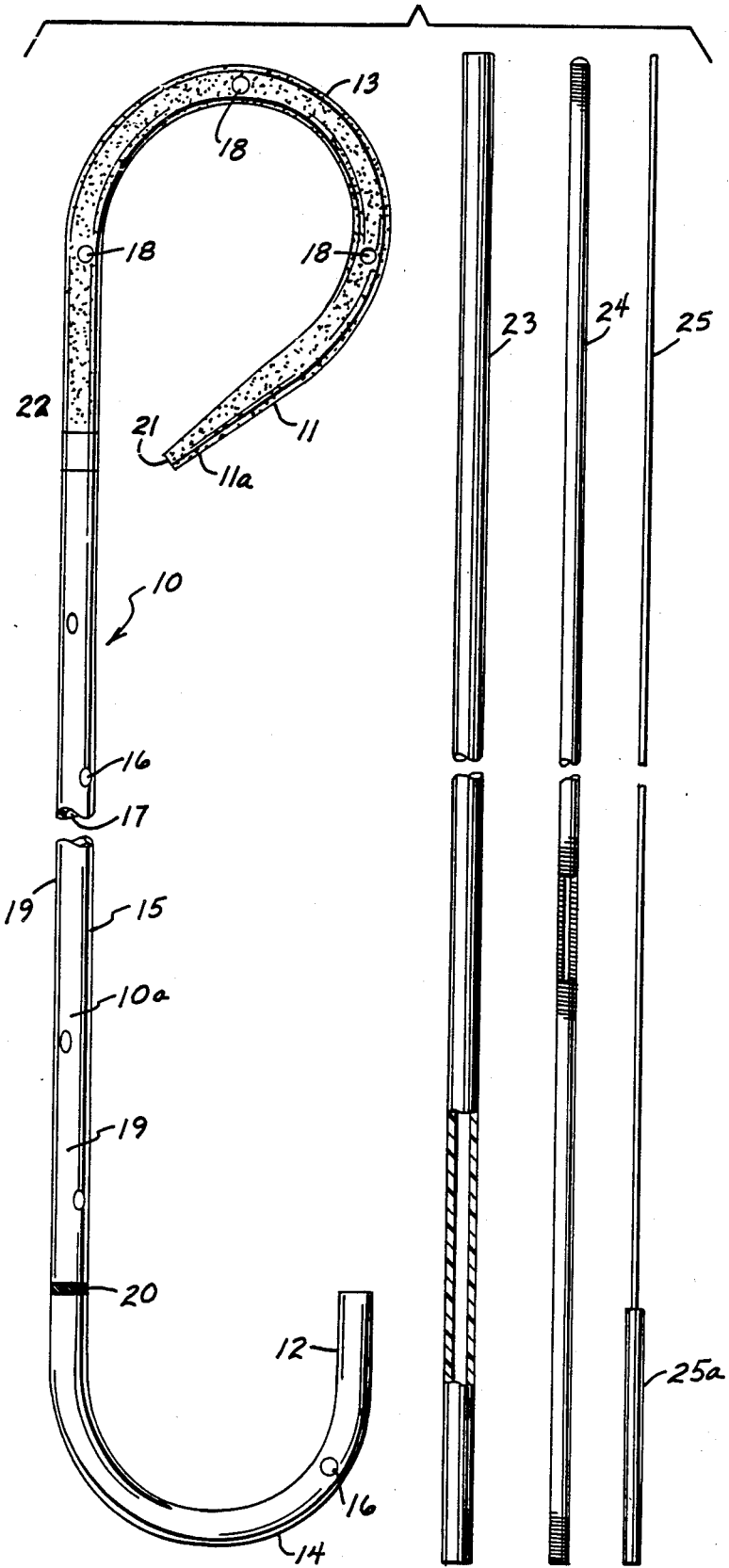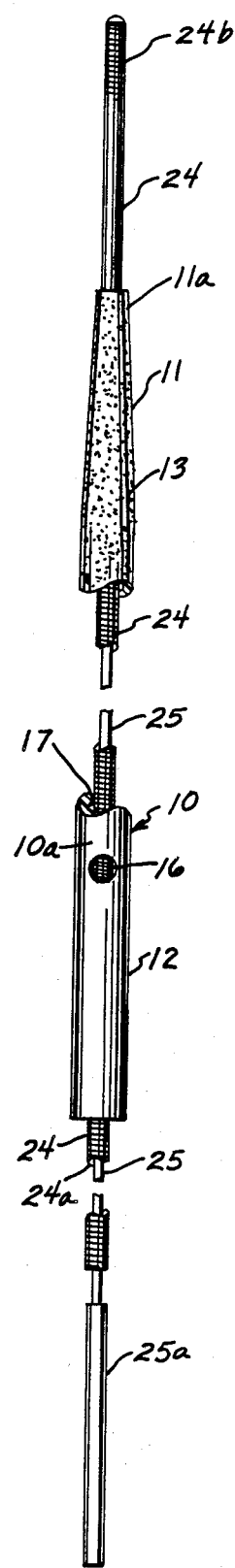
FIG. 1
FIG. 2

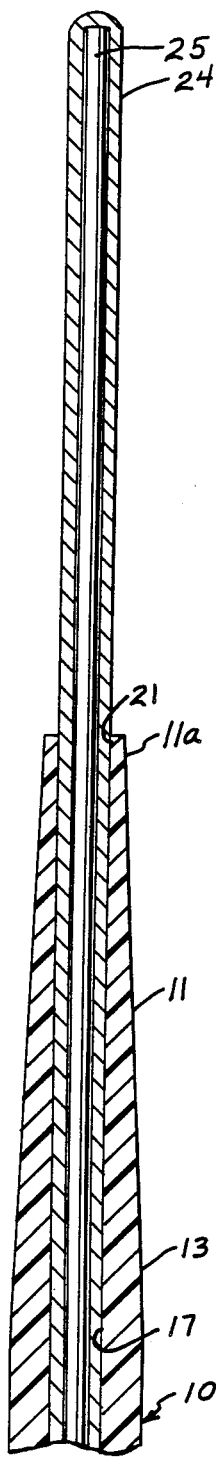
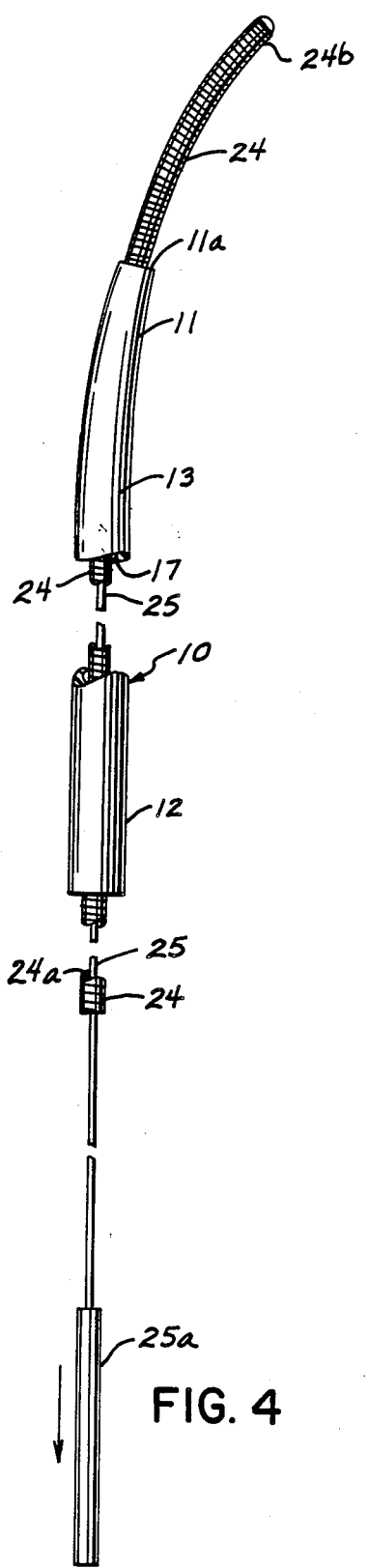
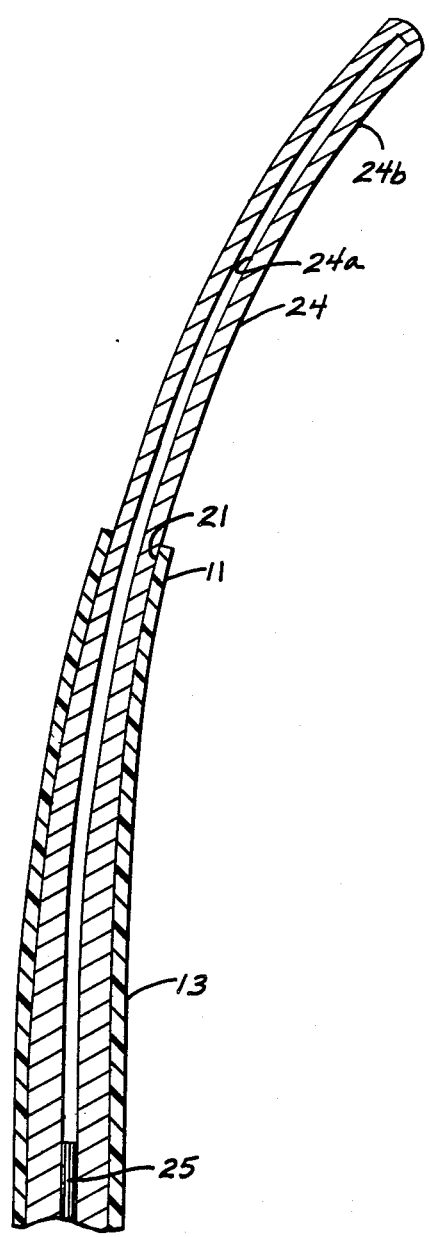
FIG. 3
FIG. 4
FIG. 5

FIG. 7
FIG. 6
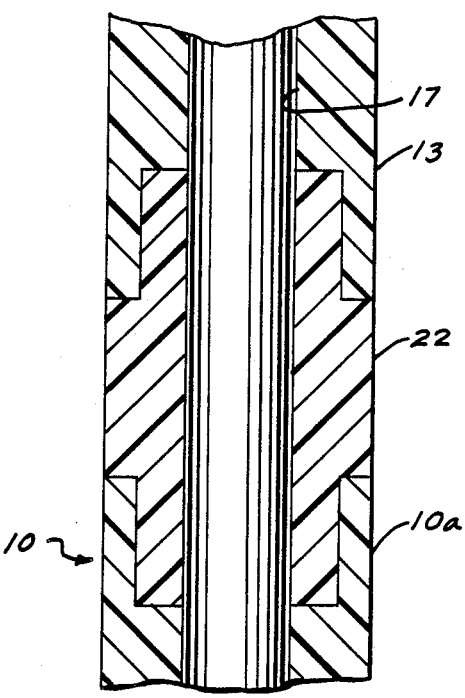
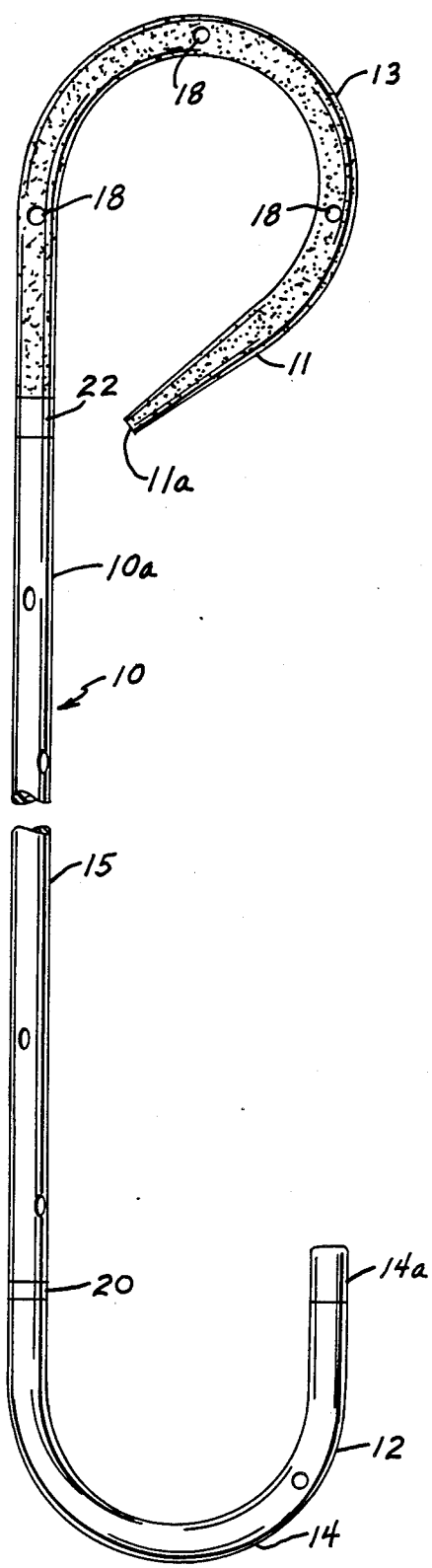
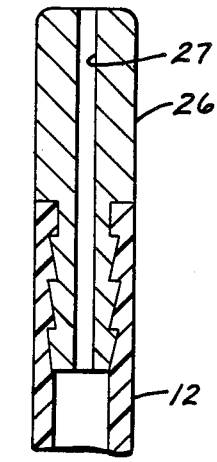
FIG. 8

URETERAL STENT SYSTEM

RELATED CASE

This application is related to copending U.S. patent application Ser. No. 091,976 filed Sept. 1, 1987 and commonly owned copending U.S. patent application Ser. No. 050,509, filed May 14, 1987.

FIELD OF THE INVENTION

The present invention relates generally to ureteral stents. More particularly, it relates to an improved ureteral stent which is less prone to migration or expulsion from the kidney.

BACKGROUND OF THE INVENTION

Indwelling ureteral catheter stents or drainage tubes have been used to bypass ureteral obstructions or uretero-vaginal fistulas and to achieve and to maintain urinary drainage between the kidney and the bladder. In the past, stents made of straight lengths of open end tubing have been used for this purpose and have provided good drainage for sustained periods of time. However, the use of such tubing has not been completely satisfactory. For example, in some instances, the tubing has migrated upward and in others it has been expelled from the kidney.

Various attempts were made to produce stents which did not have the problems which accompanied the use of such tubing. For example, stents were designed which had a hook at one end to prevent downward expulsion and which had a flange at the other end to make upward migration of the stent less likely. Another approach was to provide the body of the stent with sharply pointed barbs which were designed to prevent both downward migration and expulsion from the kidney. However, such barbs increased the diameter of the stent making it more difficult to insert.

In the Finney U.S. Pat. No. 4,212,304, issued July 15, 1979, and the Finney U.S. Pat. No. 4,307,723, issued Dec. 29, 1981, ureteral stents are disclosed which are soft silicone members which have hooks at each end and which are surprisingly effective in preventing both upward migration and downward expulsion. In normal use the proximal hook is placed in the lower calyx of the kidney or the renal pelvis of the patient and the distal hook is placed in the bladder. The stent then provides a passage for urine from the kidney to the bladder. The Finney stents are widely accepted because they work well; they are well tolerated by the patients; and they can be easily introduced both endoscopically and during open surgery.

In the Densow U.S. Pat. No. 4,610,657, a modification of a Finney-type stent is disclosed which has a hook at each end, a central lumen and a reduced opening at the proximal end. The stent can be placed in a patient using a pusher wire or by the known over-the-wire technique. The guidewire system disclosed for use with the Densow stent comprises two separate guidewires. One of the wires is the pusher wire. It is smaller in diameter than the lumen of the stent, but has a proximal end which is larger than the reduced opening at the proximal end. It is used to push the stent in place when no obstructions are encountered. The other wire is used when an obstruction is encountered. It is smaller in diameter than both the first wire and the reduced opening in the stent. When an obstruction is encountered the stent and the pusher wire are withdrawn and the pusher wire is removed. The smaller diameter wire is inserted in the lumen of the stent and the stent and wire reinserted; the leading end of the smaller wire is then advanced out the reduced opening in the proximal end and maneuvered past the obstruction. The stent is then run over the wire past the obstruction. Once the leading end of the stent is past the obstruction, the stent is pushed into place with a stent pusher.

In the Carter U.S. Pat. No. 4,713,049 a guide system is disclosed which can be used with either the Finney or Densow type stents. The guide system is comprised of a relatively flexible outer member with a flexible forgiving tip and a relatively rigid movable core which fits within the outer member. Methods of inserting stents using that guide system are described in the Carter patent.

The Finney stent and the Densow modification are both made entirely of relatively soft material, such as silicone rubber, and are widely accepted because they are well tolerated, they do not migrate upwardy and they do not cause patient discomfort. However, on occasion such stents may be expelled downwardly out of the kidney. The Finney patent suggests that the hooks could be reinforced by the incorporation of "plastic, fabric, metal or other suitable material" to make them less flexible and more resistant to migration but the incorporation of such foreign materials can detract from the otherwise good memory of the stent material.

Stents have been made of stiffer less flexible material, such as polyethylene, in efforts to reduce explusion or migration, but those stents have not been as well accepted because a stent made of stiffer material can cause bladder irritation and other patient discomfort.

It would be desirable to have a stent that had all the advantages of the Finney and the Densow stents and which, in addition, would have a greater resistance to being expelled from the kidney.

BRIEF SUMMARY OF THE INVENTION

It is an object of the present invention to disclose an improved ureteral stent which resists migration or expulsion from the kidney.

The stent of the present invention differs from the described prior art stents in that the main body is of soft and flexible material, but the proximal hook that is placed in the kidney is of a stiffer, homogenous thermoplastic material which possesses a good memory that enables it to return to its molded shape quickly at body temperature when a deforming force is removed.

The stent of the present invention is made of a material or materials having two different stiffnesses or durometers. The durometer of the proximal hook portion which curls into the kidney is relatively stiff, preferably about 95 Shore A, and that of the remainder of the stent is more flexible and soft, preferably about 50 to about 85 Shore A.

The stent of the present invention may take a variety of forms, including, a Finney type stent with a closed proximal end or an open proximal end. The guide system preferred for use with the stent of the present invention is that of the Carter patent.

The above stated and other objects and advantages of the invention will be apparent from the description which follows:

DESCRIPTION OF THE DRAWINGS

FIG. 1 is an elevational view of a kit which includes one embodiment of a stent of the present invention and a guide system;

FIG. 2 is an elevational view showing the stent and guide system of FIG. 1 with the hooks of the stent straightened;

FIG. 3 is an enlarged sectional view of the proximal end of the stent of FIG. 2;

FIG. 4 is a view similar to FIG. 2 but showing the unreinforced leading end of the guide system extending out of the stent;

FIG. 5 is a partial view, in section 1, of the unreinforcing leading end shown in FIG. 4;

FIG. 6 is an enlarged sectional view showing the junction of the stiffer proximal hook portion and the remainder of the stent of FIG. 1;

FIG. 7 is an elevational view of another embodiment of the stent of the present invention; and FIG. 8 is an enlarged sectional view of the distal end of the stent of FIG. 7.

DESCRIPTION OF THE PREFERRED EMBODIMENT

In the preferred embodiment of the invention shown in FIG. 1, there is seen a stent 10 which is an elongated tubular member having a proximal end 11 and a distal end 12. Portions adjacent each of the ends 11 and 12 of the stent 10 are formed and set in the shape of hooks 13 and 14. In the stent 10 both the proximal end 11 and the distal end 12 as shown are open. In some cases, it may be preferred to supply the stent 10 with the distal end 12 closed and an opening (not shown) in the side wall which is sized to receive the guide system.

In the drawing the hook portions 13 and 14 are shown extending in the same direction. However, the hook portions 13 and 14 preferably extend in opposite directions so that when the stent 10 is used as an indwelling ureteral stent the proximal end 11 can hook into the lower calyx of the kidney or renal pelvis while the distal end 12 curves into the bladder.

The stent 10 includes a relatively straight intermediate section 15 which extends between the proximal hook portion 13 and the distal hook portion 14.

Referring now to FIGS. 1 to 5, it can be seen that the stent 10 has radial drainage passages 16 which connect the lumen 17 of the stent 10 to the outside and permit inside/outside drainage. The drainage passages 16 are preferably spirally located about 5 centimeters apart on both sides of the straight section 15. There are similar openings 18 in the wall of the proximal hook portion 13. The stent 10 also has increment markings 19 every 5 cms and an axial ring 20 which signals the physician to stop advancing the stent when the ring reaches the ureteral orifice.

As seen best in FIGS. 3 and 5, the proximal end 11 has an externally tapered tip 11a which eases the progress of the stent 10 through the ureter of the patient and assists in the reduction of tissue trauma as the stent is advanced through the urinary tract. The opening 21 of the tip 11a is about 0.041 inches so that the stent 10 can be advanced over a standard 0.039 inch guidewire for a standard retrograde, over-the-wire placement.

The stent as described so far is similar to the Densow stent and that described in copending application Ser. No. 091,976.

The ureteral stent 10 of the present invention differs from the prior art stents in that the proximal hook portion 13 is made of a homogenous, thermoplastic material which is substantially stiffer than the soft, more flexible material from which the remainder of the stent is formed. For example, the main body 10a of stent 10 is made of a soft flexible material, preferably polyurethane, which has a durometer between about 50 and about 85 Shore 'A' to which barium sulfate has been added as the radiopaque agent. In contrast, the proximal hook portion is made of a stiffer less flexible material, also preferably polyurethane, having a durometer of about 95 Shore 'A'. The higher durometer material of the proximal hook portion 13 forms a more secure curl into the kidney thus further minimizing migration or explusion.

The hook portion 13 and main body 10a of the stent 10 can be joined together in a number of ways. The preferred method comprises modifying the ends of the proximal hook portion 13 and the main body of the stent 10 to be joined by enlarging their internal diameters and placing the thus modified ends on a wire in a mold (neither shown) about ⅛ inch apart. The gap between the ends of the proximal hook portion 13 and the remainder of the stent 10 is then filled with a polyurethane material 22 which is molded about the ends and the wire and cured to join the two pieces together as seen in FIG. 6 to form an integral stent. The stent 10 is then removed from the mold and the wire removed from lumen 17 of the stent.

Referring back to FIG. 1, there can be seen the preferred guide system of the present invention. As seen therein, the guide system comprises a stent pusher 23, a relatively large diameter hollow guide member 24, which is Teflon coated and sized to fit in the lumen 17 of the stent 10; and a longer, smaller diameter core 25 which is sized to fit within the lumen 24a of the hollow guide member 24.

To properly place the stent 10 in a patient, the physician first properly places a cystoscope in the patient. The guide system comprising the relatively large diameter hollow guide member 24 with the core 25 in the lumen 24a (as seen in FIG. 2) is next passed up the urethra. As the guide system enters the ureter, the physician advances and retracts the movable inner core 25 (as seen in FIGS. 3, 4 and 5) to regulate the softness or firmness of the tip 11a. Adjusting the tip 11a will aid in negotiating tortuous ureters and bypassing obstructions. As the leading end of the guide system enters the kidney, the physician can move the inner core 25 so that the tip 11a of the guide system gently or firmly enters the calyces. The physician then threads the stent 10 over the guide system to straighten the proximal and distal hook portions 13 and 14, respectively, as seen in FIG. 2. Using the stent pusher 23, the stent 10 is advanced over the guide system. The tapered tip 11a of the stent 10 eases its way along the guide system, assisting in the reduction of trauma to the tissue of the ureter. The spiral pattern of holes 16 placed along the shaft of the stent 10 helps to minimize kinking as the stent advances over the guide member 24. The physician can verify that the hooks form in the appropriate directions when the guide wire is removed by observing the position of a medial line (not shown) on the stent. The physician measures the progress of the stent 10 by using the increment markings 19. Also, the physician can use the increment markings 19 to define the position of obstructions. The physician also can use the axial ring 20 to aid in effectively placing the distal hook 14 within the bladder. As soon as the guide system is retracted from the proximal end, the proximal hook portion 13 curls and positions itself in the kidney. The stronger durometer of the proximal hook portion 13 minimizes movement as the guide system is retracted from the lumen 17 of the stent. As the guide system is retracted further down the shaft, the coating on the guide member aids in its smooth removal. As the guide system leaves the distal hook portion 14, the soft distal hook resumes its shape. The contour and softness of the distal hook portion 14 permit it to rest comfortably within the bladder and minimizes bladder irritation. The physician then removes the cystoscope and the stenting procedure is complete.

When it is desired to replace an indwelling stent of the type shown in FIG. 1 to 6, the stent is first cystoscopically visualized and then a foreign body forceps or a retractable type stone basket (neither shown) is advanced through the cystoscope to catch the end 12 of the stent and to retract the stent 10 from the patient.

A second embodiment of the stent of the present invention is shown in FIGS. 7 and 8. It differs from the embodiment of FIGS. 1 to 6 only in that the distal hook portion 14 includes a tip 14a which is a cylinder 26 of magnetically attractable material. The cylinder 26 has a central bore 27 through which the guide system can be introduced and is best seen in FIG. 8. The stent of FIGS. 7 and 8 can be removed with a retrieving catheter (not shown) equipped with a magent. It is disclosed and claimed in copending U.S. patent application Ser. No. 050,509.

The stent 10 is preferably formed by extruding a length of tubing of the desired size and durometer to form the main body 10a. The length of tubing is then placed in a form and heated to shape the distal hook portion 14. The openings 16 and 18 may be formed in the main body 10a at any step of the process by piercing the wall of the tubing with a flattened, sharpened hole cutter of the desired size or by use of a laser or any other conventional means. The proximal hook portion 13 is extruded of a stiffer material. The hook and tapered open proximal end 11a are formed in a heated mold. The proximal hook portion 13 is then joined to the main body 10a as described.

The material of which the stent 10 is preferably made is an extrudable polyurethane which can be characterized as being an essentially linear, segmented aliphatic polyurethane elastomer. The polyurethane is composed of three repeating units, a diol, a diisocyanate and a macroglycol. The relationship of these three repeating units to each other determine the physical characteristics of the polymer including the durometer. For example, the soft, flexible polyurethane for the main body 10a which has a durometer of about 80 Shore A has a ratio of diol to macroglycol of one to one. Since the diisocyanate links both the diol and the macroglycol there are two diisocyanates for each diol or macroglycol in this example. The stiffer polyurethanes having a durometer of about 95 Shore 'A' (60 Shore 'D') have a ratio of diol to glycol of 1.3 to 0.7 and a number of diiocyanate units that is greater than or equal to the combined number of diols and macroglycols. This polyurethane material being aliphatic and polyether based with 100% urethane linkages in the molecular backbone exhibits superior flexural life and a high degree of biocompatibility. In addition, the polymer if homogenous and not contaminated with reinforcing fibers or fillers possesses good memory and enables the proximal hook portion 13 to quickly regain its hook shape at body temperature (98.6° F.). These polymers are available from Thermedics, Inc. of Woburn, Mass. under the trade name TECOFLEX. The preparation of the polymers is described in U.S. Pat. Nos. 4,447,590 and 4,523,005, which are incorporated by reference herein.

The polyurethane material that is used to make the junction 22 (seen best in FIG. 6) is a moldable polyurethane that forms good secure bonds with both the soft material of the main body 10a and the stiffer material of the proximal hook portion 13. Polyurethanes that can be used include the polyurethane used to make the proximal hook 13 as well as other known polyurethane adhesives.

The preferred hollow guide member 24 is a tubular member having a relatively flexible forgiving tip leading end 24b which is closed. The preferred guide member 24 has an OD of about 0.032 inches; ID of about 0.016 inches and it is formed of stainless steel coated with Teflon.

The core 25 is sized to fit within the lumen 24a and is more rigid than the guide member 24. It may be formed of stainless steel wire. It preferably has an OD of about 0.013 inches. The length of the core 25 should be greater than that of the guide member 24 so that the handle 25a will protrude from the guide member 24 when the leading end 25b is seated against the closed end of the lumen 24a of the guide member 24. The handle 25a is used to advance or retract the core 25.

The stent of the present invention will normally be supplied in a kit comprising a stent 10 and the guide system. However, the stent 10 also may be sold separately for use with a standard 0.038 inch guidewire.

In the preferred embodiment described and shown in the drawing, the proximal and distal end portions of the stent are both in the form of gently curved, closed hooks. However, it is to be understood that the term "hook" is intended to include other functionally equivalent shapes such as coils which prevent migration and do not increase the effective outer diameter of the stent, or complicate its method of introduction.

The preferred method of preparing the stent of the present invention is that which has been described. However, a stent might be prepared by other methods such as extending and forming a stent extirely of soft, flexible material and thereafter stiffening the proximal hook by leaching plasticizer therefrom or coating it with more material and increasing its thickness. Likewise, use of connectors to joining the proximal hook portion to the main body of the stent is less desirable since the connectors may increase the outside diameter of the stent or reduce the size of the lumen or fail.

It will be readily apparent to those skilled in the art that a number of modifications and changes can be made without departing from the spirit of the invention. Therefore, it is to be understood that the scope of the invention is not be be limited by the foregoing description, but only by the claims.

We claim:

1. In a ureteral stent comprising an elongated member having a soft, flexible main body with a first hook at one end for placement in the bladder of a patient and a second hook at the other end for placement in the patient's kidney, the improvement which comprises forming said stent of a homogeneous, essentially linear, segmented aliphatic polyurethane elastomer cmposed of three repeating units, a diol, a diisocyanate and a macroglycol, the main body and first hook of said stent having a durometer of about 50 to about 80 Shore "A" and the second hook having a durometer of about 95 Shore "A" and a good memory that enables it to quickly resume its hook shape at body temperature when a hook straightening force has been removed.

* * * * *